(12) United States Patent  
Yazicioglu et al.

(10) Patent No.: US 8,914,099 B2  
(45) Date of Patent: Dec. 16, 2014

(54) BIOMEDICAL ACQUISITION SYSTEM WITH MOTION ARTIFACT REDUCTION

(71) Applicant: IMEC, Leuven (BE)

(72) Inventors: Refet Firat Yazicioglu, Leuven (BE); Sunyoung Kim, Leuven (BE)

(73) Assignee: IMEC, Leuven (BE)

( * ) Notice: Subject to any disclaimer, the term of this patent is extended or adjusted under 35 U.S.C. 154(b) by 0 days.

(21) Appl. No.: 13/671,050

(22) Filed: Nov. 7, 2012

(65) Prior Publication Data

US 2013/0116577 A1    May 9, 2013

Related U.S. Application Data

(60) Provisional application No. 61/557,060, filed on Nov. 8, 2011.

(51) Int. Cl.
| | | |
|---|---|---|
| *A61B 5/04* | (2006.01) | |
| *A61B 5/00* | (2006.01) | |
| *A61B 5/0402* | (2006.01) | |
| *A61B 5/053* | (2006.01) | |
| *H01L 27/08* | (2006.01) | |
| *H03F 1/56* | (2006.01) | |
| *H03F 3/45* | (2006.01) | |

(52) U.S. Cl.
CPC ........... *A61B 5/7214* (2013.01); *A61B 5/04017* (2013.01); *A61B 5/0402* (2013.01); *A61B 5/0531* (2013.01); *H01L 27/0811* (2013.01); *H03F 1/56* (2013.01); *H03F 3/45475* (2013.01); *H03F 2200/213* (2013.01); *H03F 2200/261* (2013.01); *H03F 2203/45538* (2013.01); *H03F 2203/45544* (2013.01); *H03F 2203/45548* (2013.01); *H03F 2203/45576* (2013.01)
USPC ........................................................ 600/509

(58) Field of Classification Search
None
See application file for complete search history.

(56) References Cited

U.S. PATENT DOCUMENTS

| | | | | |
|---|---|---|---|---|
| 5,238,001 A | * | 8/1993 | Gallant et al. | ................. 600/513 |
| 7,489,958 B2 | * | 2/2009 | Diab et al. | .................... 600/322 |

(Continued)

FOREIGN PATENT DOCUMENTS

| | | |
|---|---|---|
| CN | 101422362 A | 5/2009 |
| EP | 2298164 A2 | 3/2011 |
| WO | WO2009/017413 A1 | 2/2009 |

OTHER PUBLICATIONS

Hong, Sunjoo et al., "A Combined Method to Reduce Motion Artifact and Power Line Interference for Wearable Healthcare Systems", Circuits and Systems (APPCCAS), 2010 IEEE Asia Pacific Conference, Dec. 6-9, 2010, pp. 508-511.

(Continued)

*Primary Examiner* — Eric D. Bertram
*Assistant Examiner* — Elizabeth K So
(74) *Attorney, Agent, or Firm* — McDonnell Boehnen Hulbert & Berghoff LLP

(57) ABSTRACT

A system for the analysis of ECG signals is disclosed. The system may comprise (i) at least one readout channel, configured to receive an analog ECG signal acquired from at least one electrode attached to a body, and to extract an analog measured ECG signal and analog electrode-skin impedance signals; (ii) at least one ADC, configured to convert those extracted analog signals at the readout channel into digital signals; (iii) a digital adaptive filter unit, configured to calculate a digital motion artifact estimate based on said digital versions of the measured ECG signal and the electrode-skin impedance signals; (iv) at least one DAC, configured to convert said digital motion artifact estimate into an analog signal; and (v) a feedback loop for sending said analog motion artifact estimate signal back to the readout channel configured to deduct said analog motion artifact estimate signal from said analog measured ECG signal.

12 Claims, 3 Drawing Sheets

(56) References Cited

U.S. PATENT DOCUMENTS

| | | |
|---|---|---|
| 2001/0021813 A1* | 9/2001 | Yonce .......................... 600/509 |
| 2003/0171661 A1 | 9/2003 | Tong |
| 2003/0189466 A1 | 10/2003 | Kitamura |
| 2006/0097811 A1 | 5/2006 | Nakamura et al. |
| 2006/0208816 A1 | 9/2006 | Ohshima et al. |
| 2007/0142735 A1 | 6/2007 | Shin et al. |
| 2007/0268272 A1 | 11/2007 | Perski et al. |
| 2009/0066433 A1 | 3/2009 | Yamamoto |
| 2010/0315102 A1 | 12/2010 | Portmann |
| 2011/0267212 A1 | 11/2011 | Denison |
| 2013/0113549 A1 | 5/2013 | Helleputte |

OTHER PUBLICATIONS

European Search Report, European Patent Application 12191680.3 dated Mar. 7, 2013.

Kim, Sunyoung et al., "A 2.4uA Continuous-Time Electrode-Skin Impedance Measurement Circuit for Motion Artifact Monitoring in ECG Acquisition Systems", 2010 Symposium on VLSI Circuits/ Technical Digest of Technical Papers, Jun. 16, 2010, pp. 219-220.

* cited by examiner

BIOMEDICAL ACQUISITION SYSTEM WITH MOTION ARTIFACT REDUCTION

CROSS-REFERENCE TO RELATED APPLICATIONS

This application claims priority under 35 U.S.C. §119(e) to U.S. Provisional Patent Application Ser. No. 61/557,060, filed on Nov. 8, 2011, and entitled "Biomedical Acquisition System for Evaluating and Detecting Biopotential Electrical Signals", the full disclosure of which is incorporated herein by reference.

BACKGROUND

1. Technical Field

The present disclosure is related to the measurement and analysis of biopotential electrical signals, such as electrocardiogram (ECG) signals and more specifically to a biomedical acquisition system with motion artifact reduction.

2. Technical Background

Monitoring over a given period of time of biopotential electrical signals, such as an electrocardiogram (ECG), may be used, for example, to evaluate the heart condition of a patient. Recently, there has been a growing interest in wearable/portable biopotential monitoring systems, to be used, for example, in ambulatory monitoring of ECG signals, which require, for example, low power dissipation, high signal quality, small implementation area and/or robust operation during use. Especially the latter is emerging as a major problem since in real-life ambulatory conditions motion artifacts will disturb and potentially saturate the readout channel, which can make the interpretation of the ECG signal difficult. In addition, requirements for biomedical acquisition systems require even more functionality with minimal power dissipation.

OVERVIEW OF THE DISCLOSURE

According to an example embodiment of the present disclosure, a system for the analysis of ECG signals is provided. The example system comprises: (i) at least one readout channel, configured to receive an analogue ECG signal acquired from at least one electrode attached to a body, and to extract an analogue measured ECG signal and analogue electrode-skin impedance signals; (ii) at least one ADC, configured to convert those extracted analogue signals at the readout channel into digital signals; (iii) a digital adaptive filter unit, configured to calculate a digital motion artifact estimate based on said digital versions of the measured ECG signal and the electrode-skin impedance signals; (iv) at least one DAC, configured to convert said digital motion artifact estimate into an analogue signal; and (v) a feedback loop for sending said analogue motion artifact estimate signal back to the readout channel configured to deduct said analogue motion artifact estimate signal from said analogue measured ECG signal. According to an example embodiment, the analogue electrode-skin impedance signals comprise an analogue in-phase electrode-skin impedance signal, and an analogue quadrature electrode-skin impedance signal.

According to still another example embodiment, the digital adaptive filter unit comprises a digital adaptive filter that uses electrode-skin impedance signals as a reference to reduce motion artifacts from the measured ECG signal. According to still another example embodiment, the digital adaptive filter comprises a LMS filter.

According to an example embodiment, the readout channel further comprises a current source configured to inject current into the received analogue ECG signal leads to facilitate the extraction of the analogue electrode-skin impedance signals.

According to an example embodiment, the readout channel comprises an analogue gain amplifier at an analogue ECG readout module configured to deduct the analogue motion artifact estimate signal from the analogue measured ECG signal. According to an example embodiment, the analogue gain amplifier is a programmable gain amplifier which uses a differential difference amplifier architecture to accomplish subtraction of the analogue motion artifact estimate signal from the analogue measured ECG signal. According to another example embodiment, the analogue gain amplifier is a programmable gain amplifier which has a reference input to determine the input DC signal level and configured to apply the analogue motion artifact estimate signal to said reference input to accomplish deduction of the analogue motion artifact estimate signal from the analogue measured ECG signal.

According to an example embodiment, analogue analysis and treatment of ECG signals, such as deducting said analogue motion artifact estimate signal from said analogue measured ECG signal, is performed in an analogue application-specific integrated circuit (ASIC), and digital analysis and treatment of ECG signals, such as calculating a digital motion artifact estimate, is performed in a microprocessor unit, said ASIC and said microprocessor unit configured to communicate with each other. According to another example embodiment, the system comprises a digital interface comprising decimation filters for the at least one ADC and configured to multiplex digitized outputs onto a single serial peripheral interface (SPI) output, the digital interface further comprising a secondary single SPI input for driving the at least one DAC.

According to still yet another example embodiment, the ADC is a successive approximation ADC.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

The disclosure will be further elucidated by means of the following description and the appended figures. Various exemplary embodiments are described herein with reference to the following figures, wherein like numerals denote like entities. The figures described are schematic and are non-limiting. Further, any reference signs in the claims shall not be construed as limiting the scope of the present disclosure. Still further, in the different figures, the same reference signs refer to the same or analogous elements.

DETAILED DESCRIPTION

Figure 1:
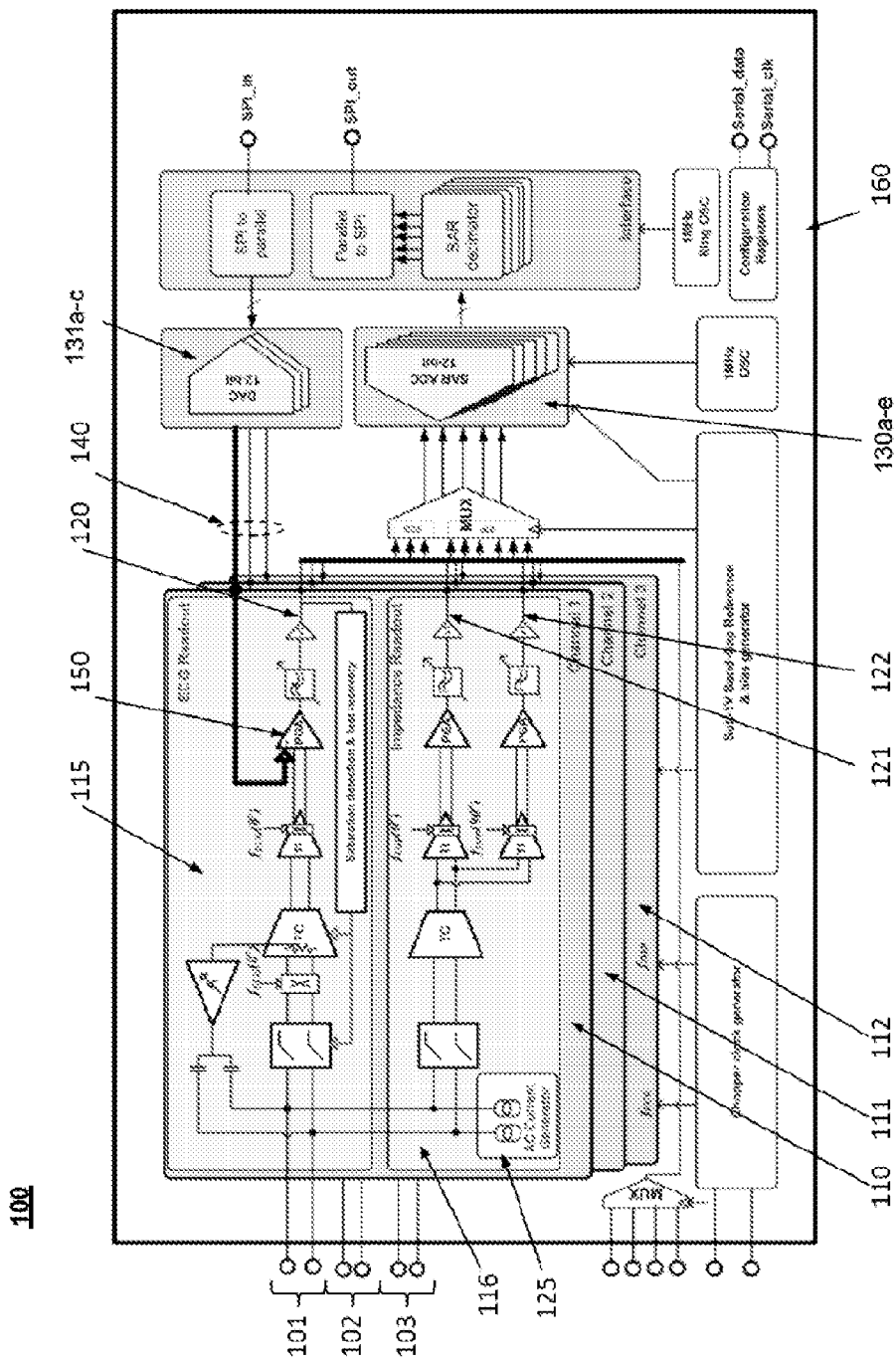
FIG. 1 shows a first exemplary block diagram of a biomedical acquisition system according to an example of the present disclosure.

FIG. 1 shows a first example embodiment of a multi-channel biomedical acquisition system 100 according to the disclosure, capable of actual real-time motion artifact suppression before the ADC. The system 100 comprises three readout channels 110, 111, 112 configured for receiving ECG signals 101, 102, 103 from corresponding electrodes attached to a body. Each readout channel 110, 111, 112 includes an ECG readout module 115 for extracting a measured ECG signal 120 and an impedance readout module 116 for extracting an electro-tissue impedance (ETI) signal, both an in-phase electrode-skin impedance signal 121, and a quadrature electrode-skin impedance signal 122. A current source 125 is also integrated in the readout channels to inject current into the ECG leads to facilitate the measurement of the ETI. The outputs (plus any extra sensors) of each readout module of the biomedical acquisition system are digitized by five SAR ADCs 130a-e, which can be selectively operated at an oversampling mode (8 kSps/chn) or standard mode (500 Sps/chn). The outputs of the ADCs 130a-e are time-multiplexed on a master SPI output line. According to an example embodiment of the disclosure, the outputs of the impedance readout module 116 are post-processed and sent through three DACs 131a-c and corresponding feedback lines 140, back to the ECG readout module 115 in order to accomplish motion artifact suppression.

According to an example embodiment of the disclosure, the SAR-ADCs 130a-e convert ten analog signals, three ECG signals, and six ETI signals and one extra analog input. The outputs of the SAR-ADCs are mainly used to aid motion artifact estimation. The system 100 also includes three sigma-Delta ADCs (not shown). Once the analog waveforms of a motion artifact estimate are generated (one for each readout channel), the motion artifact estimate is fed back, with the use of three DACs 131a-c, negatively to the ECG readout modules and is deducted or subtracted from the measured ECG signal, for example at a programmable gain amplifier (PGA) 150, in order to reduce the measured ECG signal amplitude, for example at the output of the PGA 150. In this way a lower resolution ADC is needed for processing the measured ECG signal, which leads to lower power consumption and smaller area overhead.

According to an example embodiment of the disclosure, a digital interface is incorporated for implementing the decimation filters for the ADCs and for multiplexing all the digitized outputs, from each readout channel, onto a single SPI output. A secondary single SPI input is used to deliver digital filter output to the DACs. The output SPI operates in master mode, while the input SPI operates in slave mode. The generation of the various clocks for each readout channel is derived from a single input clock (~32 kHz), wherein said input clock is generated externally. A chopper clock generator derives the various clock signals (2 kHz chopper, 4 kHz bias and 8 kHz ripple filter) from the externally generated input clock. The band-gap reference generates a stable reference voltage. The bias generator derives the various bias currents and voltages from the band-gap reference voltage. The sample clock of the SAR ADC is generated by a first on-chip oscillator; the oscillator in this case generates a clock signal of 1 MHz. A second ring oscillator is also incorporated to generate the SPI output clock, in this case also 1 MHz. This oscillator consumes less power and can be turned on and off quickly to save power when no data needs to be pushed on the SPI bus.

According to an example embodiment of the disclosure, to store the various configuration modes of the biomedical acquisition system 100 a number of configuration registers are implemented in the form of serially programmable shift register.

Figure 2:
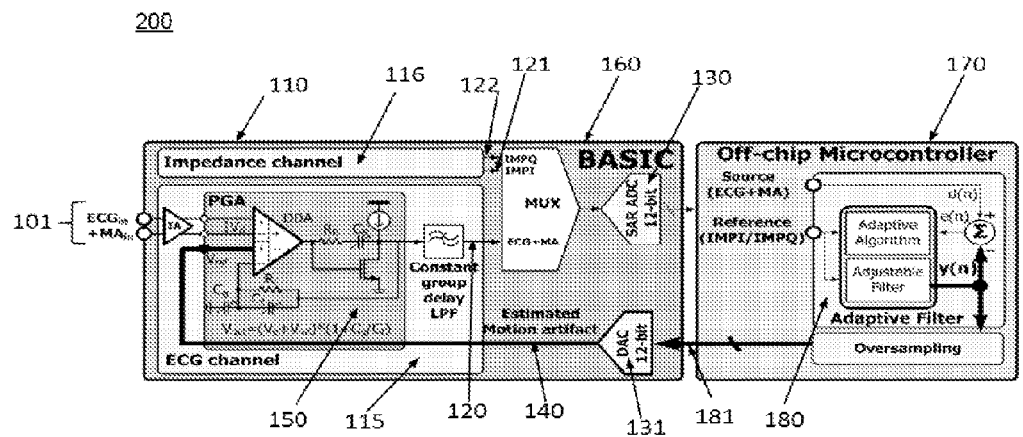
FIG. 2 shows a second exemplary block diagram of a biomedical acquisition system according to an example of the present disclosure.

According to an example embodiment of the disclosure, a biomedical acquisition system 200 may be implemented, for example, as an ASIC or as a bio-potential acquisition ASIC (BASIC) 160 in combination with a microcontroller (μC) or microprocessor 170 configured to digitally process signals received from the BASIC 160, as shown in FIG. 2. According to an example embodiment, the BASIC 160 communicates with the microcontroller 170, to send and receive data. The microcontroller 170 may also, for example, supply a clock (e.g. 32 kHz) and/or a control signal (e.g. serial_data/serial_clk) to program the BASIC 160 in the desired mode of operation. According to another example embodiment, the microcontroller 170 may, for example, receive SPI data packets (16 bit), representing the digitized data as well as a time reference packet. According to an example embodiment, the microcontroller may comprise a digital adaptive filter unit 180 configured to calculate a motion artifact estimate 181 based on input digitized versions of the measured ECG signal 120 and the in-phase electrode-skin impedance signal 121, and the quadrature electrode-skin impedance signal 122, and send the motion artifact estimate 181, for example through an SPI data bus, back to the BASIC 160.

According to an example embodiment of the disclosure, the digital adaptive filter unit 180 may be implemented in hardware and/or software. According to another embodiment of the disclosure the digital adaptive filter unit 180 may implement or run, for example, a Least Mean Square (LMS) filter. The LMS filter estimates the motion artifact on the readout channel 110 based on the ETI signals. The motion artifact estimate 181 is fed back to the BASIC 160 through a DAC 131 and a feedback line 140, and the DAC output is deducted or subtracted from the measured ECG before final amplification by the PGA 150 of the ECG readout module 115. According to another example embodiment of the disclosure, the PGA 150 uses a Differential Difference Amplifier (DDA) architecture to accomplish the subtraction.

According to another example embodiment, the digital adaptive filter unit 180 may implement or run any other type of filter which uses electrode skin impedance signals as a reference (that have maximum correlation with the motion artifact signal and minimal correlation with the ECG signal) to reduce the motion artifact from the ECG signals. According to another example embodiment, statistical analysis algorithms, such as ICA (Independent Component Analysis) or PCA (Principal Component Analysis) algorithms can be used to remove motion artifacts in digital domain.

According to an example embodiment of the disclosure, the biomedical acquisition system 200 achieves reduction or suppression of the motion artifact signals present in the measured ECG signal 120 by reducing said motion artifact signals in the analogue domain, prior to final amplification and prior to analogue to digital conversion of the measured ECG signal 120. According to an example embodiment of the disclosure, said suppression of the motion artifact signals is performed with the aid of adaptive filtering in the digital domain. According to another example embodiment, the biomedical acquisition system is capable of actual real-time motion artifact suppression before the ADC 130.

Figure 3:
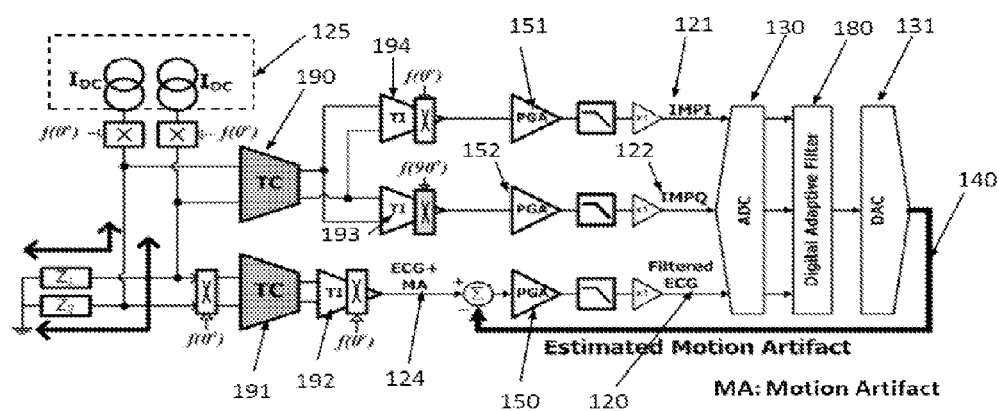
FIG. 3 shows a third exemplary block diagram of a biomedical acquisition system according to an example of the present disclosure.

FIG. 3 shows another schematic view of an example biomedical acquisition system 300 according to the present disclosure, comprising a current source 125, two transconductance amplifiers 190, 191, three transimpedance amplifiers 192, 193, 194, three programmable gain amplifier 150, 151, 152, an analogue to digital converter (ADC) 130, a digital adaptive filter unit 180, and a digital to analogue converter (DAC) 131.

According to an example embodiment of the disclosure, the digital adaptive filter unit 180 extracts the estimated motion artifact from the reference signals (the in-phase electrode-skin impedance (IMPI) signal 121 and the quadrature-phase electrode-skin impedance (IMPQ) signal 122) and the measured ECG signal 120. Then, the extracted motion artifact estimate is converted to an analog signal through the DAC 131 and sent back, through feedback loop 140, to the input of the PGA 150 in the ECG readout module in order to reduce the motion artifact in the analog domain.

According to an example embodiment of the disclosure, at a first instance, the measured ECG signal 120 comprises the received ECG signal with a motion artifact signal (ECG+MA). The electrode-skin impedance signals 121, 122 and the ECG signal with motion artifact signal (ECG+MA) are measured simultaneously. These measured analog signals are then converted to digital signals and processed using the digital adaptive filter unit 180, which then generates a digital motion artifact estimate, and said digital motion artifact estimate is converted to an analogue signal and feedback to the input of the PGA 150. The PGA 150 then performs a first coarse motion artifact reduction by deducting or subtracting the motion artifact estimate signal from ECG signal with motion artifact signal (ECG+MA). At a second instance, the measured ECG signal 120 at the output of the PGA 150 is processed again at the digital adaptive filter unit 180 to calculate a more accurate digital motion artifact estimate which later on enables a finer motion artifact reduction. Therefore, a coarse and a fine motion artifact reduction is advantageously possible with one DAC.

According to an example embodiment of the disclosure, the output signal of the PGA 150 only includes the ECG signal without the motion artifact signal, which significantly reduces the dynamic range requirements of the ADC leading to power and area reduction of the system.

According to another example embodiment of the disclosure, the motion artifact is reduced in the analog domain before the ADC, which advantageously prevents ECG channel saturation in analog domain and ECG signal loss. Therefore, the measured ECG signal can be preserved without information loss due to a large motion artifact signal. Furthermore, the motion artifact signal can be reduced in front of the ADC which reduces the required resolution for the ADC, thus leading to reduction of the power consumption and ADC area.

According to another example embodiment of the disclosure, the PGA has a reference input to determine the input DC level, the estimated motion artifact signal can be applied to this reference input of the PGA and therefore eliminating the need of an analog subtraction block for the feedback signal.

According to another example embodiment of the disclosure, the PGA has a gain higher than one, and the feedback system doesn't require additional gain stage, which eliminates the need for extra power consumption and area.

According to another example embodiment of the disclosure, real time motion artifact reduction is achieved in the analog domain without extra sensors. To reduce the motion artifact, digital adaptive filter requires reference signal which has high correlation with motion artifact and low correlation with target ECG signal. By measuring electrode-skin impedance and use it as a reference signal for the digital adaptive filter, the system doesn't need any extra sensors for the digitally assisted analog motion artifact reduction.

According to another example embodiment of the disclosure, the BASIC is implemented in CMOS technology.

According to yet another example embodiment of the present disclosure, a method for the analysis of ECG signals is provided. For example, the method may include at least one readout channel receiving an analogue ECG signal acquired from at least one electrode attached to a body, and extracting an analogue measured ECG signal and analogue electrode-skin impedance signals. The method may then include at least one ADC converting those extracted analogue signals at the readout channel into digital signals. Further, the method may involve a digital adaptive filter unit calculating a digital motion artifact estimate based on said digital versions of the measured ECG signal and the electrode-skin impedance signals. Still further, the method may involve at least one DAC converting said digital motion artifact estimate into an analogue signal. Yet still further, the method may involve a feedback loop sending said analogue motion artifact estimate signal back to the readout channel configured to deduct said analogue motion artifact estimate signal from said analogue measured ECG signal. It should be explicitly noted that many possibilities and permutations described above with respect to the system described above may equally apply to the method for the analysis of ECG signals.

Further example embodiments and advantages will be described below.

According to an example embodiment of the disclosure, the present disclosure describes a biomedical acquisition system for the evaluation and detection of dynamically changing biopotential electrical signals, such as ECG signals.

According to still another embodiment of the present disclosure a biomedical acquisition system is provided, configured for monitoring dynamically changing biopotential electrical signals, such as the ambulatory monitoring of Electrocardiogram (ECG). The system may comprise the following features: at least one readout channel, each configured for receiving the ECG signal acquired by at least one electrode attached to the biological subject body; at least one successive approximation register (SAR) analog to digital converter (ADC), configured for converting two analog signals and can operate in standard mode or oversampled mode; at least one sigma-delta ADC configured for converting the ECG signal received by the electrodes; at least one Digital-to-Analogue Converters (DAC) for generating the analog waveforms of the motion artifact estimate, said motion artifact estimate being fed back negatively to the ECG readout channels; a digital interface configured for implementing decimation filters for the ADCs and for multiplexing all the digitized outputs onto a single serial peripheral interface (SPI) output, said digital interface may also include a secondary single SPI input for driving the plurality of DACs; a chopper clock generator for generating the clock signals for each readout channel; a band-gap and bias generation circuit for generating the biasing currents and voltages; a first oscillator for generating a sample clock signal, wherein said clock signal is connected to the SAR-ADC; a second oscillator for generating the SPI output clock signal; at least one configuration register configured for storing the various configuration settings of the biopotential acquisition system.

According to another example embodiment of the present disclosure, an ASIC communicates via an SPI output and SPI input with a micro-controller to send and receive data. The microcontroller supplies the clock (32 kHz) and serial_data/serial_clk to program the ASIC in the desired mode of operation. It receives 16 bit SPI data packets, representing the digitized data as well as a time reference packet. The microcontroller will run a motion artifact estimation algorithm and sends the motion artifact estimates on a separate SPI data bus back to the ASIC.

According to another example embodiment of the present disclosure, each readout channel of the biopotential system further comprises: an ECG readout channel for extracting the ECG signal; an Impedance readout channel for extracting the electro-tissue impedance (ETI); a current source for injecting current into the ECG leads to measure the ETI.

According to still another example embodiment, the channel outputs (plus any extra sensor inputs) are digitized by the plurality of SAR ADCs, which can be selectively operated at an oversampling mode or standard mode. The outputs of the ADCs are time-multiplexed on a master SPI output line. The outputs of the ETI channels are post-processed and fed back to the ECG channels through the plurality of DACs to accomplish Motion artifact suppression.

According to still another example embodiment, to enhance the signal quality the Biomedical acquisition system includes an Instrumentation Amplifier (IA) with a fully integrated low frequency High Pass Filter (HPF), which is capable of achieving a very high-mode rejection ration (CMRR) while also being able to reject large DC electrode offset (DEO). The HPF may be implemented with fully-integrated DC-blocking capacitors, which allow rail-to-rail DEO rejection. As a result the proposed integrated HPF allows for the compensation of parasitic mismatch and maximizes the CMRR to 120 dB. The resistance of the HPF can be realized by the switched-cap resistors, to provide the DC-bias and the differential input impedance.

According to still another example embodiment, the biomedical acquisition system also includes a smart saturation detection block and fast recovery circuit to facilitate quick start-up and immediate recovery from channel saturation. According to another example embodiment, the BASIC comprises a smart saturation detection block and fast recovery circuit to facilitate quick start-up and immediate recovery from channel saturation. A dynamic clocked comparator checks the channel output. If it is continuously saturated for at least 160 ms, the IA inputs are briefly shorted to the IA DC-bias voltage, temporarily altering the HPF characteristics. Similarly, the time constants of the offset compensation loops are also reduced. The output is recovered after only 200 ms despite the 200 mHz HPF. The system is not trigger if the channel is briefly saturated (i.e. strong QRS-complex). Once the system has detected saturation and has reset the channels, the whole saturation detection block is shut down for 1s. This is to avoid continuous resets.

According to an example embodiment of the disclosure, the instrumentation amplifier (IA) is the first one able to achieve a fully integrated 200 mHz High-Pass Filter (HPF) capable of rail-to-rail DC-offset rejection without compromising the CMRR (120 dB). Finally, a configurable ADC resolution and support for external sensors such as accelerometers and temperature sensors further enable the use of the BASIC for multi-modal information acquisition.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

The invention claimed is:

1. A system for the analysis of electrocardiogram (ECG) signals, the system comprising:
at least one readout channel, configured to receive an analogue ECG signal acquired from at least one electrode attached to a body, and to extract analogue signals comprising an analogue measured ECG signal and analogue electrode-skin impedance signals;
at least one analogue to digital converter (ADC), configured to convert the extracted analogue signals at the readout channel into digital signals;
a digital adaptive filter unit, configured to calculate a digital motion artifact estimate based on said digital versions of the measured ECG signal and the electrode-skin impedance signals;
at least one digital to analogue converter (DAC), configured to convert said digital motion artifact estimate into an analogue motion artifact estimate signal; and
a feedback loop for sending said analogue motion artifact estimate signal back to an analogue ECG readout module within the readout channel, wherein the analogue ECG readout module is configured to deduct said analogue motion artifact estimate signal from said analogue measured ECG signal.

2. The system according to claim 1, wherein said analogue electrode-skin impedance signals comprise (i) an analogue in-phase electrode-skin impedance signal and (ii) an analogue quadrature electrode-skin impedance signal.

3. The system according to claim 1, wherein the digital adaptive filter unit comprises a digital adaptive filter that uses electrode-skin impedance signals as a reference to reduce motion artifacts from the measured ECG signal.

4. The system according to claim 3, wherein the digital adaptive filter comprises a Least Mean Square (LMS) filter.

5. The system according to claim 1, wherein the readout channel further comprises a current source configured to inject current into received analogue ECG signal leads to facilitate the extraction of the analogue electrode-skin impedance signals.

6. The system according to claim 1, wherein the analogue ECG readout module comprises an analogue gain amplifier configured to deduct the analogue motion artifact estimate signal from the analogue measured ECG signal.

7. The system according to claim 6, wherein the analogue gain amplifier is a programmable gain amplifier which uses a differential difference amplifier architecture to accomplish subtraction of the analogue motion artifact estimate signal from the analogue measured ECG signal.

8. The system according to claim 6, wherein the analogue gain amplifier is a programmable gain amplifier that has a reference input to determine an input DC signal level and configured to apply the analogue motion artifact estimate signal to said reference input to accomplish deduction of the analogue motion artifact estimate signal from the analogue measured ECG signal.

9. The system according to claim 1, wherein analogue analysis and treatment of ECG signals is performed in an analogue application-specific integrated circuit (ASIC), and wherein digital analysis and treatment of ECG signals is performed in a microprocessor unit, said ASIC and said microprocessor unit configured to communicate with each other.

10. The system according to claim 9, wherein the system comprises a digital interface comprising decimation filters for the at least one ADC and configured to multiplex digitized outputs onto a single serial peripheral interface (SPI) output, the digital interface further comprising a secondary single SPI input for driving the at least one DAC.

11. The system according to claim 1, wherein the ADC is a successive approximation ADC.

12. The system according to claim 9, wherein the analogue analysis and treatment of ECG signals comprises deducting said analogue motion artifact estimate signal from said analogue measured ECG signal, and wherein the digital analysis and treatment of ECG signals comprises calculating the digital motion artifact estimate.

\* \* \* \* \*